US00PP21384P2

(12) United States Plant Patent
Bergman

(10) Patent No.: US PP21,384 P2
(45) Date of Patent: Oct. 12, 2010

(54) ***CHRYSANTHEMUM* PLANT NAMED 'SUNNY YOMISTIQUE'**

(50) Latin Name: *Chrysanthemum×morifolium*
Varietal Denomination: Sunny Yomistique

(75) Inventor: Wendy Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,546

(22) Filed: Sep. 24, 2009

(51) Int. Cl.
*A01H 5/00* (2006.01)

(52) U.S. Cl. ..... Plt./295

(58) Field of Classification Search ..... Plt./295
See application file for complete search history.

*Primary Examiner*—Annette H Para
(74) *Attorney, Agent, or Firm*—S. Matthew Edwards

(57) ABSTRACT

A new *Chrysanthemum* plant named 'Sunny Yomistique,' particularly distinguished by the small single yellow ray florets, compact and short, uniform habit with excellent branching, and dark, glossy small foliage.

1 Drawing Sheet

Latin name of the genus and species of the plant claimed: *Chrysanthemum×morifolium.*

Varietal denomination: 'Sunny Yomistique'.

BACKGROUND OF THE NEW PLANT

The present invention comprises a new *Chrysanthemum*, botanically known as *Chrysanthemum×morifolium,* and hereinafter referred to by the variety name 'Sunny Yomistique.'

The new cultivar has small single yellow ray florets, compact and short, uniform habit with excellent branching, and dark, glossy small foliage.

'Sunny Yomistique' is a product of a planned breeding program. 'Sunny Yomistique' originated as a natural whole plant mutation of 'Frosty Yomistique,' U.S. Plant Pat. No. 20,224.

'Sunny Yomistique' was discovered and selected by the inventor as a single flowering plant within a population of the parent cultivar, grown out doors in a field covered by saran in Fort Myers, Fla., in February 2007.

The parent cultivar 'Frosty Yomistique' has white with a slight pink hue flower color and lighter foliage color.

The first act of asexual reproduction of 'Sunny Yomistique' was accomplished when vegetative cuttings were propagated from the initial selection in May 2007, in a controlled environment in Fort Myers, Fla.

Horticultural examination of plants grown from cuttings of the plant initiated in May 2007, and continuing thereafter, has demonstrated that the combination of characteristics as herein disclosed for 'Sunny Yomistique' are firmly fixed and are retained through successive generations of asexual reproduction.

'Sunny Yomistique' has not been observed under all possible environmental conditions. The phenotype may vary significantly with variations in environment such as temperature, light intensity and day length.

A Plant Breeder's Right for this cultivar was applied for in Canada in October 2008. 'Sunny Yomistique' has not been made publicly available more than one year prior to the filing of this application.

BRIEF DESCRIPTION OF THE PHOTOGRAPHS

The accompanying photographic drawing shows typical flower and foliage characteristics of 'Sunny Yomistique' with colors being as true as possible with an illustration of this type. The photographic drawing shows 3 flowering potted plants of the new variety, with a close-up of the flowers.

DETAILED BOTANICAL DESCRIPTION

The plant descriptions, measurements and aforementioned photographs were taken in Gilroy, Calif. in early April 2009, in greenhouse conditions. The plants were started and grown in central coastal California, then shipped to Gilroy, Calif. in early April 2009. Plants were grown under conditions which approximate those generally used in commercial potted chrysanthemum production and were about 8-9 weeks of age.

Color references are made to The Royal Horticultural Society Colour Chart (R.H.S.) 2001.

BRIEF SUMMARY OF THE INVENTION

The following traits have been repeatedly observed and are determined to be basic characteristics of the new variety. The combination of these characteristics distinguishes this *Chrysanthemum* as a new and distinct variety.

TABLE 1

DIFFERENCES BETWEEN THE NEW VARIETY 'SUNNY YOMISTIQUE' AND A SIMILAR VARIETY

| | 'Sunny Yomistique' | 'Yolisette' (U.S. Plant Pat. No. 13,030) |
|---|---|---|
| Flower color | Yellow | Darker yellow |
| Flowering response | 6 weeks | 7 weeks |
| Growth habit | Compact | More vigorous |

Plant

*Form, growth and habit.*—Herbaceous pot-type, short and compact habit, stems upright and outwardly spreading, freely branching,

*Plant height.*—13-15 cm.
*Plant height (inflorescence included).*—14-16 cm.
*Plant width.*—10 cm.
*Quantity of short days to flowering (response time).*—39-42 days.

Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 137C.
*Lower surface.*—RHS 137C.
*Mature, leaf color, upper surface.*—Closest to RHS 137C.
*Lower surface.*—RHS 137C.
*Length.*—5.3-5.8 cm.
*Width.*—2.7-2.9 cm.
*Shape.*—Ovate.
*Base shape.*—Attenuate.
*Apex shape.*—Mucronulate.
*Margin.*—Palmately lobed; slightly serrate.
*Texture, upper surface.*—Bi-fid T-shaped hairs.
*Lower surface.*—Bi-fid T-shaped hairs.
*Color of veins, upper surface.*—RHS 146C.
*Color of veins, lower surface.*—RHS 146C.
*Petiole color.*—RHS 146C.
*Length.*—0.8-1.1 cm.
*Diameter.*—0.2 cm.
*Texture.*—Bi-fid T-shaped hairs.

Stem:
*Quantity of main branches per plant.*—3-4 with lots of secondary.
*Quantity of leaves per branch.*—4-6.
*Color of stem.*—RHS 146B but appears lighter with the bi-fid hairs.
*Length of stem.*—7-8 cm.
*Diameter.*—0.2-0.3 cm.
*Length of internodes.*—0.5-0.7 cm.
*Texture.*—Bi-fid T-shaped hairs.
*Color of peduncle.*—RHS 146B.
*Length of peduncle.*—3.5-4.7 cm.
*Peduncle diameter.*—0.1-0.15 cm.
*Texture.*—Bi-fid T-shaped hairs.

Inflorescence:
*Type.*—Composite type, solitary inflorescences (daisy-type) borne terminally above foliage, ray florets arranged acropetally on a capitulum.
*Blooming habit.*—Excellent year round performance.
*Quantity of inflorescences per plant.*—8-12.
*Lastingness of individual blooms on the plant.*—About 35 days.
*Fragrance.*—Slight.

Bud (just before opening/showing color):
*Color.*—RHS 7A to RHS 7B.
*Length.*—0.7-0.9 cm.
*Width.*—0.6-0.7 cm.
*Shape.*—Oblate.

Immature inflorescence:
*Diameter.*—2.6-2.7 cm.
*Color of ray florets, upper surface.*—Closest to RHS 1C with RHS 144A basally.
*Lower surface.*—RHS 5D.

Mature inflorescence:
*Diameter.*—3.2-2.7 cm.
*Total diameter of 'disc'.*—1.4-1.5 cm.

Ray florets:
*Quantity of florets.*—19-25.
*Color of florets, upper surface.*—RHS 4C.
*Lower surface.*—RHS 5D.
*Length (cm).*—1.3-1.8 cm.
*Width.*—0.4 cm.
*Shape.*—Oblong to elliptical.
*Apex shape.*—Emarginate to praemorse.
*Margin.*—Entire.
*Texture, upper surface.*—Papillose.
*Lower surface.*—Papillose.

Disc florets:
*Average quantity of florets.*—100-150.
*Color of florets.*—RHS 1C; RHS 13B apex.
*Length.*—0.5 cm.
*Width.*—0.1 cm.
*Shape.*—Tubular, enlongated.
*Apex shape.*—Acute, 5 pointed.

Phyllaries:
*Quantity.*—About 15-20.
*Color, upper surface.*—RHS 138A.
*Lower surface.*—RHS 138A.
*Length.*—0.3-0.4 cm.
*Width.*—0.1 cm.
*Shape.*—Lanceolate.
*Apex shape.*—Obtuse.
*Based.*—Fused.
*Margins.*—Entire.
*Texture.*—Bi-fid T-shaped hairs.

Reproductive organs:
*Pistil.*—1.
*Length.*—0.6 cm.
*Style color.*—RHS 1B to RHS 1C.
*Style length.*—0.5 cm.
*Stigma color.*—RHS 14B.
*Stigma shape.*—Bi-parted.
*Ovary color.*—RHS 155C.
*Stamens.*—1.
*Color of filaments.*—RHS 1B to RHS 1C.
*Length filaments.*—0.3 cm.
*Anther color.*—RHS 13B.
*Color of pollen.*—RHS 14A.
*Pollen amount.*—Moderate.
*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Sunny Yomistique,' substantially as illustrated and described herein.

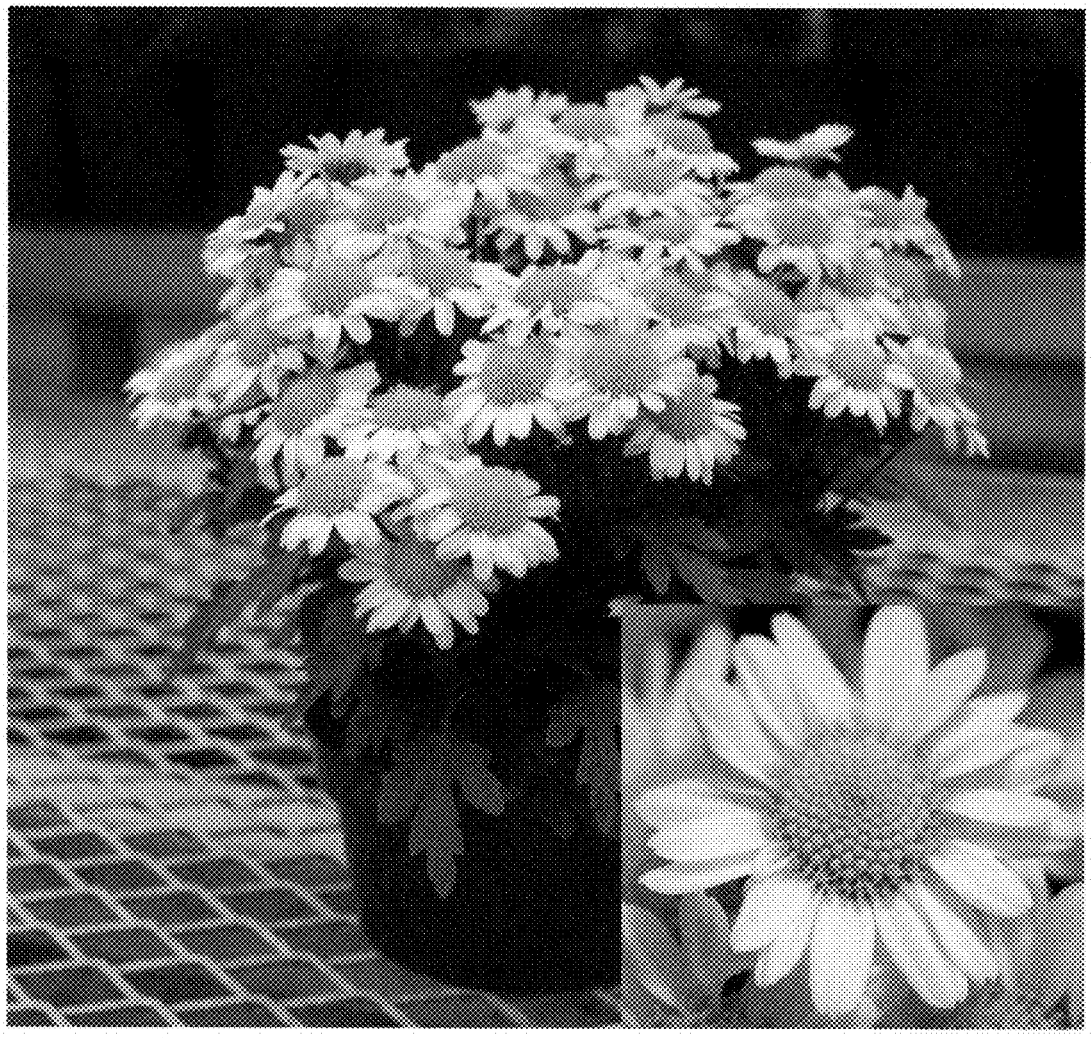

* * * * *